United States Patent
Mayer et al.

(10) Patent No.: US 10,719,921 B2
(45) Date of Patent: Jul. 21, 2020

(54) METHOD AND SYSTEM FOR PROVIDING A LOCALLY-CONSISTENT ENHANCEMENT OF A LOW-QUALITY IMAGE

(71) Applicants: TEL HASHOMER MEDICAL RESEARCH, INFRASTRUCTURE AND SERVICES LTD., Ramat Gan (IL); RAMOT AT TEL-AVIV UNIVERSITY LTD., Tel Aviv (IL)

(72) Inventors: Arnaldo Mayer, Ramat Hasharon (IL); Michael Green, Rehovot (IL); Nahum Kiryati, Tel Aviv (IL); Edith M. Marom, Tel Aviv (IL); Eli Konen, Tel Aviv (IL)

(*) Notice: Subject to any disclaimer, the term of this patent is extended or adjusted under 35 U.S.C. 154(b) by 0 days.

(21) Appl. No.: 16/097,285

(22) PCT Filed: May 4, 2017

(86) PCT No.: PCT/IL2017/050497
§ 371 (c)(1),
(2) Date: Oct. 29, 2018

(87) PCT Pub. No.: WO2017/191643
PCT Pub. Date: Nov. 9, 2017

(65) Prior Publication Data
US 2019/0139202 A1 May 9, 2019

Related U.S. Application Data (60) Provisional application No. 62/408,786, filed on Oct. 16, 2016, provisional application No. 62/331,521, filed on May 4, 2016.

(51) Int. Cl.
*G06T 5/00* (2006.01)
*G06K 9/62* (2006.01)
(Continued)

(52) U.S. Cl.
CPC ............ *G06T 5/008* (2013.01); *G06K 9/3241* (2013.01); *G06K 9/40* (2013.01); *G06K 9/4642* (2013.01);
(Continued)

(58) Field of Classification Search
CPC .................................................. G06T 3/4053
See application file for complete search history.

(56) References Cited

U.S. PATENT DOCUMENTS 5,867,555 A 2/1999 Popsecu et al.
8,396,325 B1* 3/2013 Kwatra ..................... G06T 7/33
382/284

(Continued)

FOREIGN PATENT DOCUMENTS

WO 2016008956 1/2016

OTHER PUBLICATIONS

International Search Report and Written Opinion dated Sep. 28, 2017 for PCT/IL2017/050497 filed May 4, 2017.
(Continued)

*Primary Examiner* — Gandhi Thirugnanam
(74) *Attorney, Agent, or Firm* — Chernoff Vilhauer LLP (57) ABSTRACT

A method of providing a medical image of a ROI of a patient, the method comprising: acquiring a first medical image of a region of interest (ROI) of a patient, the medical image characterized by a first signal to noise ratio (SNR); determining for a given pixel in the first image a plurality of different first image patches in the first image, each having a pixel that is coincident with the given pixel; determining for each first image patch a similar second image patch having a second SNR greater than the first SNR; determining an enhanced pixel value for the given pixel having an enhanced SNR greater than the first SNR responsive to pixel values of pixels in the determined second image patches;
(Continued)

and using the determined pixel value to generate a second medical image of the ROI having an enhanced SNR greater than the first SNR.

8 Claims, 5 Drawing Sheets

(51) Int. Cl.

| | | |
|---|---|---|
| *G06K 9/46* | (2006.01) | |
| *G06K 9/40* | (2006.01) | |
| *G06K 9/32* | (2006.01) | |
| *G06T 7/00* | (2017.01) | |
| *G16H 30/20* | (2018.01) | |

(52) U.S. Cl.
CPC ......... *G06K 9/6215* (2013.01); *G06K 9/6276* (2013.01); *G06T 5/002* (2013.01); *G06T 7/0012* (2013.01); *G16H 30/20* (2018.01); *G06K 2209/051* (2013.01); *G06T 2207/10072* (2013.01); *G06T 2207/10116* (2013.01); *G06T 2207/10121* (2013.01)

(56) References Cited

U.S. PATENT DOCUMENTS

| | | | | |
|---|---|---|---|---|
| 8,582,916 | B2* | 11/2013 | Bar-Aviv | G06T 5/20 382/128 |
| 9,123,140 | B1* | 9/2015 | Liu | G06T 3/4053 |
| 9,317,903 | B1* | 4/2016 | Liu | G06T 3/4053 |
| 2004/0218834 | A1 | 11/2004 | Bishop et al. | |
| 2006/0290950 | A1* | 12/2006 | Platt | G06T 3/4053 358/1.2 |
| 2010/0272340 | A1* | 10/2010 | Bar-Aviv | G06T 5/20 382/131 |
| 2012/0155728 | A1* | 6/2012 | DeMan | G06T 11/006 382/131 |
| 2012/0328210 | A1* | 12/2012 | Fattal | G06T 3/403 382/264 |
| 2013/0034299 | A1* | 2/2013 | Lin | G06T 3/4053 382/162 |
| 2013/0071040 | A1* | 3/2013 | Jin | G06T 3/4053 382/254 |
| 2014/0254882 | A1* | 9/2014 | Jin | G06T 7/248 382/107 |
| 2015/0023611 | A1* | 1/2015 | Salvador | G06T 3/4053 382/263 |
| 2015/0104116 | A1* | 4/2015 | Salvador | G06T 3/4053 382/300 |
| 2015/0110386 | A1* | 4/2015 | Lin | G06T 5/002 382/159 |
| 2015/0154766 | A1* | 6/2015 | Goshen | G06T 3/4053 382/131 |
| 2016/0027152 | A1* | 1/2016 | Hsieh | G06T 5/00 382/254 |
| 2016/0180502 | A1* | 6/2016 | Salvador Marcos | G06T 3/4053 382/155 |
| 2019/0139202 | A1* | 5/2019 | Mayer | G06T 5/002 |

OTHER PUBLICATIONS

International Report on Patentability dated Aug. 29, 2018 for PCT/IL2017/050497 filed on May 4, 2017.
S. Hashemi et al., Adaptively Tuned Iterative Low Dose CT Image Denoising, Hindawi Publishing Corporation, Computational and Mathematical Methods in Medicine, vol. 2015, Article ID 638568, 2015, 12 pages.
F. Pontana el al., Chest computed tomography using iterative reconstruction vs filtered back projection (Part 2): image quality of low-dose CT examinations in 80 patients. European radiology, 2011. 21(3): pp. 636-643.
M. Beister et al., Iterative reconstruction methods in X-ray CT. Physica Medica, 2012. 28(2): pp. 94-108.
S. Ha et al., Low dose CT image restoration using a database of image patches. Physics in medicine and biology, 2015. 60(2): pp. 869-880.
W. Xu et al., Efficient low-dose CT artifact mitigation using an artifact-matched prior scan. Medical physics, 2012. 39(8): pp. 4748-4760.
H. Yu, et al., Ultra-low dose lung CT perfusion regularized by a previous scan. Academic radiology, 2009. 16(3): pp. 363-373.
H. Zhang, et al., Statistical image reconstruction for low-dose CT using nonlocal means-based regularization. Computerized Medical Imaging and Graphics, 2014. 38(6): pp. 423-435.
D. Ai, et al., Adaptive Tensor-Based Principal Component Analysis for Low-Dose CT Image Denoising, PLOS ONE | DOI:10.1371/journal.pone.0126914 May 18, 2015, pp. 1-20.
K. Dabov, et al., Image denoising by sparse 3-D transform-domain collaborative filtering. Image Processing, IEEE Transactions on, 2007. vol. 16, No. 8: pp. 2080-2095.
A. Buades, et al., A non-local algorithm for image denoising. in Computer Vision and Pattern Recognition, 2005. CVPR 2005. IEEE Computer Society Conference on. 2005. IEEE.
D.E. Goldberg, Genetic algorithms in search optimization and machine learning. vol. 412. 1989: Addison-Wesley Reading Menlo Park, Chapter 3, p. 76.
C. Silpa-Anan et al., Optimised KD-trees for fast image descriptor matching. in Computer Vision and Pattern Recognition, 2008. CVPR 2008. IEEE Conference.
M. Muja et al., Fast Approximate Nearest Neighbors with Automatic Algorithm Configuration. VISAPP (1), 2009. 2.
Z. Wang, et al., Image quality assessment: from error visibility to structural similarity. Image Processing, IEEE Transactions on, 2004. 13(4): pp. 600-612.
M. Lebrun, An analysis and implementation of the BM3D image denoising method. Image Processing On Line, 2012. 2: pp. 175-213.
European Search Report prepared by the European Patent Office for EP 17792615, dated Mar. 7, 2019, 5 pages.
Boubil, David et al., "Spatially-Adaptive Reconstruction in Computed Tomography Using Neural Networks," IEEE Transactions on Medical Imaging, Jul. 1, 2015, vol. 34, No. 7, pp. 1474-1485.
Ha, Sungsoo et al., "Low Dose CT Image Restoration Using a Localized Patch Database," 2013 IEEE Nuclear Science Symposium and Medical Imaging Conference, Oct. 27, 2013, pp. 1-2.
Bastião Silva, Luís A. et al., "A PACS Archive Architecture Supported on Cloud Services," International Journal of Computer Assisted Radiology and Surgery, Jun. 16, 2011, vol. 7, No. 3, pp. 349-358.

* cited by examiner

METHOD AND SYSTEM FOR PROVIDING A LOCALLY-CONSISTENT ENHANCEMENT OF A LOW-QUALITY IMAGE

RELATED APPLICATIONS

The present application is a US National Phase of PCT Application No. PCT/IL2017/050497 filed on May 4, 2017, which claims benefit under 35 U.S.C. 119(e) of U.S. Provisional Applications 62/331,521 filed May 4, 2016 and 62/408,786 filed Oct. 16, 2016 the disclosures of which are incorporated herein by reference.

BACKGROUND

Medical imaging such as performed by a CT (computed tomography), a MRI (magnetic resonance imaging) scanner or the like, may require that a patient be scanned for a length of time during which the patient is subject to uncomfortable and/or undesirable physical and psychological conditions. The patient may have to endure not only an uncomfortably long exposure period, or an uncomfortable physical position during an exposure period, the patient may also be exposed to an undesirable amount of energy that the scanner generates to acquire the image. For example, patients very often experience psychological discomfort anticipating confinement in or being confined in an MRI imager for an extended period of time, and an amount of radiation to which a patient may be exposed during a CT scan can be dangerous to the patient's health. However, reducing patient scanning time in an MRI scanner or reducing an amount of radiation to which a patient is exposed during a CT scan generally damages quality of the image and typically reduces image SNR. Also, a prolonged scanning time or a high radiation dose do not necessarily ensure a high quality image since such an image is also dependent on other factors like, for instance, undesirable artifacts.

SUMMARY

An aspect of this disclosure relates to providing a medical imaging system ("imaging system") comprising a medical imaging device (or, in short, "imaging device") configured to acquire a relatively low-quality medical image ("L-image") of any region of interest (ROI) in a physical body and in particular, but not exclusively, a ROI of a patient, and process the L-image in order to provide an image ("E-image") which is enhanced in quality in comparison to the L-image.

The term "quality", in connection with an image in this application, means a degree to which said image is suitable for analysis and/or diagnosis and/or data gathering and/or evaluation of any kind. Moreover, in this application the term "quality" in all its forms, abbreviations, derivations etc. whether explicit or implied, does not mean or set—unless expressly stated otherwise—any specific value, level or standard and is to be understood in a relative or contextual manner.

The ROI may be any part, organ or region of the human body (where the term "body" includes any and all physical aspects of the living or dead organism of a human being or an animal, including head, trunk, limbs, internal or external organs, skins, bones, appendages, extremities etc.) and/or any section, slice, segment or fragment thereof. In specific embodiments of the disclosure, the term "ROI" may also refer to a part or the entirety of any organic or inorganic object, material or medium.

The term "image" in this application means any type of visual representation, including one-dimensional, bidimensional, tridimensional or any other kind of space or combination thereof. Additionally, the term "image" in this application, alone or in conjunction with any other term, may apply, according to the case, to one or more parts or layers of an image like, for instance, one or more slices of a CT, MRI or PET scan or to the complete set and/or composite of said slices, which form the complete scan (or, in short "scan"). Furthermore, the term "image" in this application applies, according to the case, both to raw acquisition data—for example, a CT sinogram or an MRI k-space matrix acquired by an imaging device—or the image resulting from any intermediate or final processing of said raw data.

Additionally, the term "image" in this application applies to any data that can be visually represented including, for instance, data related to sound, pressure, temperature and so forth.

In an embodiment of the disclosure the imaging system includes and/or has access to a high-quality database ("H-database") which may be located anywhere and which contains high-quality image/s ("H-image/s") and/or patch/es ("H-patch/es"), optionally extracted from said H-images and comprising relatively small regions of said H-images. The H-images and/or the H-patches, which may be stored in any convenient manner are relevant to the L-image/s and/or corresponding low-quality patches ("L-patch/es") that the imaging systems may be configured to acquire and might need to be enhanced.

The term relevant, in the context of an embodiment of the disclosure, means that the images or patches extracted from the H-database contain information that can be used to enhance the L-images or L-patches. Therefore, the H-database will typically contain images of items related to the items in L-images. For example, if an L-image of brain CT scan is to be enhanced, the H-database used for that purpose should also contain H-images and H-patches of brain CT scans. Moreover, the term relevant may also mean that the H-database used to enhance an L-image contains H-images and H-patches having a physical pixel size compatible with the L-image, L-patch, physical pixel size. If desired, adjustments of the physical pixel size may be easily performed using methods well known in the art.

Said H-image and/or H-patches—as well as L-image and or L-patches—may or may not have been acquired using the imaging system described in this disclosure and, more generally, said images may have been acquired at any point of time and/or in any sequence and/or for any patient and/or for any ROI and/or in any location and/or by any suitable means.

The imaging system may comprise a processor ("E-processor") that uses H-images or H-patches from a H-database to process L-images or L-patches of a ROI of a patient to provide an enhanced image (hereinafter "E-image") of the ROI.

A patch and a pixel in an E-image may be also referred to as "E-patch" and "E-pixel". Similarly, a pixel in a H-patch or in a L-patch may also be referred to as "H-pixel" and "L-pixel".

In the specific case that the enhancement in said E-image is obtained by achieving an enhanced SNR, which enhancement may also be referred to as "de-noising", said image may also be referred to as an "E-SNR image" or a "de-noised image". The term "E-image" also encompasses any image which undergoes, as described in this disclosure, a quality improvement—not necessarily an improvement in SNR,—in respect to a relatively low quality image (or, in short "L-image")—not necessarily a L-SNR image. A non-SNR improvement may be, the attenuation of image artifacts such, for example, streak artifacts in CT images, calcium blooming in coronary CT angiography images, or ringing artifacts in MRI images.

A process of enhancing an L-image, in accordance with an embodiment, may be carried out on pixels that belong to the L-image. A resulting image, after quality enhancement in accordance with an embodiment, may be referred to as an "E-image".

The term "processor", used interchangeably in this application with the term "E-processor", means any device, element, component or combination thereof, capable of carrying out one or more of actions according to this disclosure, in order to acquire, obtain, view, process or, in general, manage, alter, and/or manipulate an image and capable of enhancing a L-image as to obtain an E-image.

An E-processor in accordance with an embodiment of the disclosure may comprise, one or more of the following elements—a general purpose or dedicated device, a PC, a processor, a controller, circuit, an IC, any combination thereof, a biocomputer, biologically based components, biomolecular components, where the term "combination", throughout this application means, for the processor, as well as for all the other elements and/or components of the system, any possible configuration that enables the cumulative, alternative, or parallel structuring, and/or usage of hardware and/or software and/or tangible and/or intangible components and/or elements in any integration, distribution, arrangement, addition, replacement or exclusion, system, location, type of connection, material, time sequence and physical and/or virtual presence and/or distribution of the aforementioned.

In order to practice an embodiment of the disclosure the processor may carry out any operation which may, for example, be contained in, and/or provided by, one or more of the following: a program, instructions algorithm, routine, logic, rule, process flow, operation, function, process, and any combination thereof (hereinafter the "operation elements" or "enhancement operation elements") which operation elements can be, partially or entirely, implemented in at least one or any combination of more than one of the following forms: software, hardwired, printed circuit and so forth.

Accordingly, the term "processor" in this application must be understood as the processor being equipped with the necessary operation enhancement elements which may, of course, vary in different embodiments.

The term "equipped" in relation to the processor and the operation elements means, one or more of the possible ways or combinations in which the processor and the operation elements may be configured to work together including, for example, by way of inclusion, installation, integration, distribution, presence in different devices working in conjunction in any manner whatsoever, including in any type of network.

The processor may be a dedicated one or a general purpose processor equipped with the enhancement operation elements. The processor is, preferably, also capable of carrying out all standard computer activities, which include interfacing the other hardware and/or software elements of the system, peripheral devices, communication devices, networks, managing data and so forth ("standard computer activities").

It is noted that specific embodiments of the disclosure may require more than one processor working separately or in conjunction. Additionally, the processor may be, according to the embodiments, a single processor or a plurality of processors the combination of which and/or the cumulative operation of which provides the requirements and functionalities of an embodiment of the disclosure and/or standard computer activities. Operations described hereinafter are intended as being performed by the processor and/or by its mediation with other devices, unless explicitly stated otherwise.

According to an embodiment of the disclosure, in order to enhance the quality of an L-image to provide an E-image for the L-image, the processor may select a given pixel "$p_j$" to be enhanced ("the given pixel"). Then, the processor may define a patch (L-patch) of pixels that includes pixel $p_j$, which may also be referred to as a reference pixel. The subscript "j" in "$p_j$" stands for a generic pixel position—generally indicated by a value in the L-image. Obviously, when a different pixel in the L-image is considered, the value of j changes according to the pixel position. The value of j is therefore defined by $1 \leq j \leq a$ number of pixels in L-image. It goes without saying that many alternative ways for addressing a given pixel may be used. For instance, instead of defining the absolute position a pixel in the L-image, the position of a pixel may be defined as a relative position based on the pixel's position in a specific L-patch using a Patch-number index and a pixel-position index within the specific patch. However, alternative ways for addressing the pixel and/or a patch, do not change in any manner the nature of the disclosure.

For the sake of simplicity and for illustration purposes only, the L-patch is hereinafter described as a square patch and the given pixel "$p_j$" is defined as a central pixel in said L-patch but, according to an embodiment, a shape of an L-patch may vary in any convenient or desirable manner.

The L-patch extracted as an example in FIG. 3 is a square Ps×Ps patch where Ps=3, which is a shorthand for indicating a patch ("P") having a side length ("s") of three pixels and consisting of 9 pixels which can also be indicated as $P_s^2=9$. And successful experimental results have been obtained for $P_s=5$ by the inventors. For avoidance of any doubt, "side length" means the number of pixels that form said side. Also the term "size" in connection with a patch means the number of pixels contained in said patch. Thus, for instance, a square having a side length of seven pixels can be indicated as $P_s^2=49$. An alternative notation for the number of pixels can be $P_N$, in this case $P_N=49$. Moreover, the shape of a patch, according to the disclosure, is not limited to squares and a patch may be such as $P_{s1} \times P_{s2}$ whereby $s1 \neq s2$—for instance, $P_{s1}=5$, $P_{s2}=11$ and $P_{s1} \times P_{s2}=55$. Furthermore, one or more sides of the patch may consist of an even number of pixels. The verb "extract", in reference to a patch may mean "define" or "select" the patch regardless whether or not the patch is copied, cut, duplicated, deleted or other otherwise disposed of.

Furthermore, wherever applicable in specific embodiments of the disclosure, the term "pixel" in this application, may be used interchangeably or accumulatively with the term "voxel" that is, a volumetric pixel or "3D-pixel". Consequently, where applicable, a patch may be indicated as $P_s^3$, if all sides of the patch are equal (both even or odd) and may be indicated as $P_{s1}^2 \times P_{s2}$ if only two sides are of equal size or $P_{s1} \times P_{s2} \times P_{s3}$ if all sides are different for example, in a (5×7×13) patch or in a (4×9×6) patch.

Generally speaking, an embodiment in accordance with the disclosure does not require a patch to be of any specific size or shape and the patch may be of any shape suitable for the purposes of an embodiment of the disclosure. Generally any shape that tiles a region of an ROI may be advantageous. If a patch used for a specific embodiment does not contain a given pixel $p_j$ that is the central pixel in the patch, unlike in the $P_s^2=9$ patch used as example in the description of an embodiment, another pixel may be defined as a reference pixel. Whichever size or shape is used throughout the invention, the total number of pixels which forms the patch may be generally indicated in the invention as $P_N$. As for the type of pixel value ("$V(p_j)$"), this can be of any desired real, complex or other numerical type.

Now, according to the currently described embodiment of the disclosure, a patch (L-patch), around a selected given pixel $p_j$ of the L-patch is defined. Then, $P_N$ distinct patch (O-patches) that have the same size as the L-patch and contain pixel $p_j$, are defined. Where the term "distinct" means that there is no total overlap between any 2 or more O-patches. Notwithstanding the above, there may be a total overlap between a single one of the O-patches and the L-patch. After the O-patches have been determined, a corresponding H-patch for each of the O-patches is determined and extracted (or in short "returned") from a relevant H-database whereby the H-patch exhibits a degree of similarity to the corresponding O-Patch, that is, satisfies a desired similarity criterion. The H-patches are returned from the H-database so that in each specific case the size of the determined O-patch and the size of the returned H-patch are the same. In a variation of the embodiment more than one H-patch may be returned for each O-patch.

A variety of high-quality data sources ("H-source"), may be used, in addition to or instead of the H-database, for returning a H-patch for each O-patch. The returned H-patch advantageously exhibits a desired degree of similarity to the O-Patch, that is, satisfies a desired criterion. For example, the H-patch may be returned by determining an approximate nearest neighbor (ANN) of the O-patch. It is noted that the term "approximate nearest neighbor", relates to a degree of similarity between the O-patch and the H-patch, optionally, represented by one-dimensional vectors. It is noted that the ANN approach is only an exemplary approach, and many other suitable criteria, well known in the art, may be used. In addition or alternative to returning an H-patch from a H-database, an H-patch, may also be returned, from other H-sources, which can be used to provide data relevant to the L-image. For instance: a neural network after prior appropriate training. It is noted that the term "source" in this application, in relation to images and/or patches of any kind and quality and their relative databases, contains, but is not limited to, said images and/or patches and/or databases. Thus, for example, the term "H-database" is contained in the term "H-source". The H-source, L-source and E-database typically contain very large amounts of data (BIG DATA) required for image enhancement according to this disclosure, which may be best, but not exclusively, to store them in the cloud.

A set of H-patches returned for the O-patches of the pixel $p_j$ may be indicated as "$NNp_j$" or $\{NNp_j\}$ which stands for "the set of H-patches which are the approximate nearest neighbors of the O-patches extracted from the H-database or H-source. In the current example, $P_s^2=9$ patches are extracted.

It should be noted that while all the O-patches contain the given pixel value, $V(p_j)$, there is no requirement that all or even any of the H-patches returned for the O-patches contain any pixel value that is the same or close to $V(p_j)$ or, more generally, that has any degree of similarity with value $V(p_j)$, but only that each returned H-patch for the respective O-patch be considered as, optionally, entirely overlapping its respective O-patch.

Next, the processor computes an enhanced pixel value ("$\hat{p}j$") for the given pixel $p_j$ as a function of the patches belonging to $NNp_j$ as follows:

$$\hat{p}_j = F(\hat{P}_1, \ldots, \hat{P}_{P_s^2}) \text{ for } \hat{P}_i \in (NN_{p_j}), \quad (1)$$

where, $\hat{p}_j$ is, obtained by applying a function "F" on the H-patches ($\hat{P}_1, \ldots, \hat{P}_{p_s^2}$), which H-patches belong to the set $NN_{p_j}$, $F(X): \mathcal{R}^{P_s^2} \to \mathcal{R}^s$, and $i=1, \ldots, P_s^2$ Different choices may be made for function F. Below, three nonlimiting examples of the many possible choices for the function F are discussed. A simple choice of F may be the average value of all the pixels of the H-patches which share the same location as the given pixel, leading $\hat{p}_j =$ $$\frac{1}{P_s^2} \sum_{i=1}^{P_s^2} \hat{P}_{ij} \text{ for } \hat{P}_i \in (NN_{p_j}) \quad (2)$$

where $\hat{P}_{ij}$ stands for pixel value in patch $\hat{P}_i$ at the location overlapping with pixel $p_j$. In this approach, each overlapping patch $\hat{P}_i$ contributes to the enhanced value $\hat{p}_j$ via its pixel $\hat{P}_{ij}$, which is the way low-quality pixel $p_j$ is "perceived" by the H-patch $\hat{P}_i$.

Another example of possible choice for F, is to weight the contributions $\hat{P}_{ij}$, $i=1 \ldots P_s^2$ by a distance measure between $\hat{P}_i$ and the original L-patch defined around $p_j$, formalized as follows:

$$\hat{p}_j = \frac{\sum_{i=1}^{P_s^2} \exp\left(-\frac{D(P_j, \hat{P}_i)}{h^2}\right) \hat{P}_{ij}}{\sum_{i=1}^{P_s^2} \exp\left(-\frac{D(P_j, \hat{P}_i)}{h^2}\right)}, \hat{P}_i \in (NN_{p_j}), \quad (3)$$

where $h=P_s \cdot \gamma$ is a filtering parameter and $\gamma$ a constant, $\hat{P}_j$ is the L-patch defined around pixel $p_j$, and $D(P_j, \hat{P}_i)$ is the average L1 (or another Ln norm for n>1) distance between the overlapping pixels of $\hat{P}_j$ and $\hat{P}_i$. Thus, surrounding $\hat{P}_i$ H-patches with high similarity to $\hat{P}_j$ at their overlap will contribute more to the enhanced value $\hat{p}_j$, for pixel $p_j$.

Bearing in mind that pixel $p_j$ has already been defined as a two-dimensional pixel or a three-dimensional voxel, the two examples of functions F described above can be generalized as to apply to any bi-dimensional or three-dimensional patch with any number of pixels $P_N$ with any side size combination. Furthermore, said functions can be generalized as to apply to any image-source (H-source, L-source, E-source) and the respective patches of said sources, including any approximate neighbor of any bi-dimensional or three-dimensional patch. Accordingly, formula (3) can be generalized as follows:

$$\hat{p}_j = \frac{\sum_{i=1}^{P_N} \text{EXP}\left(-\frac{D(P_j, \hat{P}_i)}{P_N \cdot \beta}\right) \hat{P}_{ij}}{\sum_{i=1}^{P_N} \text{EXP}\left(-\frac{D(P_j, \hat{P}_i)}{P_N \cdot \beta}\right)}, \hat{P}_i \in (NN_{p_j}) \quad (4)$$

Where $P_N \cdot \beta > 0$ is a filtering parameter and $\beta$ is a constant. Similarly, formula (2) can be generalized as follows:

$$\hat{p}_j = \frac{1}{P_N} \sum_{i=1}^{P_N} \hat{P}_{i,j} \text{ for } \hat{P}_i \in (NN_{P_j}) \quad (5)$$

And formula (1) can be generalized as follows:

$$\hat{p}_j = F(\hat{P}_1, \ldots, \hat{P}_{P_N}) \text{ for } \hat{P}_i \in (NN_{P_j}) \quad (6)$$

Whereby $\hat{p}_j$ is obtained by applying a function "F" on the H-patches $(\hat{P}_1, \ldots, \hat{P}_{P_N})$ which H-patches belong to the set $NN_{P_j}$. where $F(X): \mathcal{R}^{P_N} \to \square$ and $i=1, \ldots, P_N$ A further example of possible choice for F is a neural network that has been trained beforehand to map H-patches, corresponding to the O-patches containing pixel $p_j$, onto an enhanced value for $\hat{p}_j$ for the pixel. It is noted that if the H-source which provided the H-patches is also a neural network, the function F in this current example of possible choice of F is a second neural network, different from the first neural network that constituted the H-source.

Now, after one of the possible F functions has been applied, the value of pixel $p_j$ ($V(p_j)$), is replaced with $\hat{p}_j$, which is the enhanced pixel value ("EPV") of $p_j$. The processor may repeat the pixel-enhancement process described above for each a plurality of different given pixels $p_j$ in the L-image in order to provide, for each of said pixels an enhanced pixel value ("EPV"), which can be used to provide an E-image based on the L-image.

In an embodiment to further boost the enhancing effect, the newly obtained E-image may be defined as an L-image$^{(1)}$ to which the image enhancement process is repeated to obtain a further enhanced E-image$^{(1)}$ and the process may be repeated n times to obtain an enhanced L-image$^{(n)}$, E-image$^{(n)}$, which may serve as an E-image for the original L-image.

As it can be appreciated from all said above, the invention object of this application makes use, among other things, of a Locally-Consistent approach whereby each one the O-patches can be considered as proposing—through its corresponding H-patch—an enhanced value of $p_j$, that fits well with neighboring pixels in the H-patch, thus promoting the preservation of spatial local-consistency. In other words, the resulting enhanced value of $p_j$ (EPV) reflects the way in which each of the O-patches perceives pixel the value $p_j$ ($V(p_j)$)

An aspect of the disclosure therefore comprises a method for providing a Locally-Consistent enhancement of a Low-Quality image (L-image) resulting in an Enhanced Image (E-image), comprising the following steps:
(i) Selecting a pixel of the L-image to be enhanced;
(ii) Defining around the selected given pixel, a patch (L-patch), whereby the given pixel is pixel $p_j$ of the L-image;
(iii) Defining $P_N$ distinct (O-patches) that have the same size as the L-patch, contain pixel $p_j$ and have a certain overlap with the L-patch; and
(iv) For each O-patch, returning from a relevant high-quality source (H-source), a high quality patch (H-patch) that exhibits a desired degree of similarity to said O-Patch, that is, satisfies a desired criterion but does not necessarily contain a pixel value that is equal or close to the value $V(p_j)$ of pixel $p_j$;
(v) Computing an enhanced pixel value (EPV) for $p_j$, which EPV enhances the quality of pixel $p_j$, by applying a function $F(\underline{X})$ to the H-patches in (iv);
(vi) Replacing the pixel value of $p_j$ with the EPV; and
(vii) If desired, repeating steps i to vii.

Figure 4:
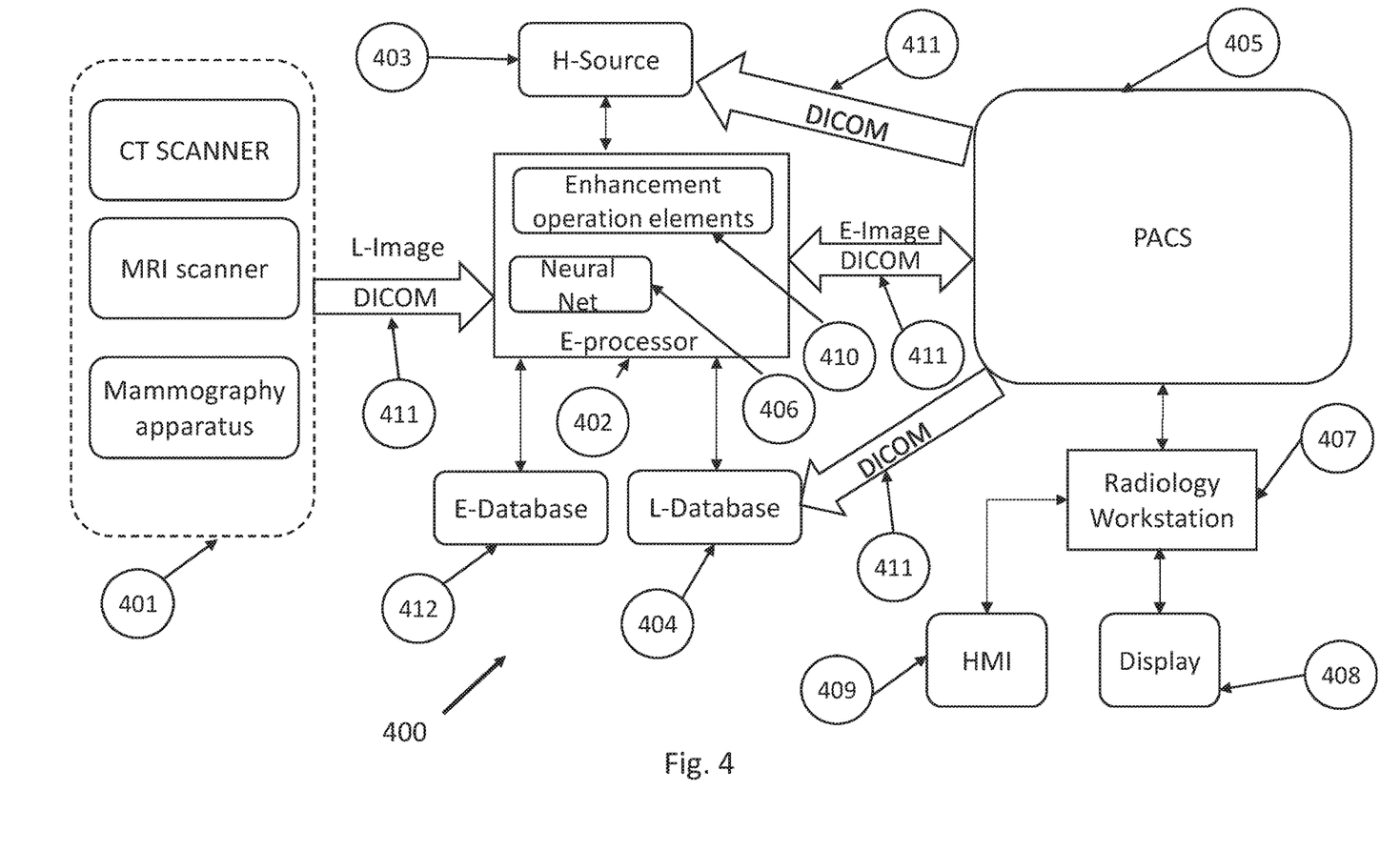
FIG. 4 schematically shows a system operable to provide enhanced quality images, E-images, based on enhancing low quality, L-images, in accordance with an embodiment of the disclosure.

According to another embodiment, the disclosure relates to a system for providing a Locally-Consistent enhancement of a Low-Quality image (L-image) resulting in an Enhanced Image (E-image). FIG. 4, schematically shows a system 400 for providing E-images of L-images in accordance with an embodiment of the disclosure. System 400 optionally comprises an E-processor (402) interfaced to an H-database (403) and an L-database (404). The E-processor (402) in this embodiment may be a PC communicating with a PACS (Picture Archiving and Communication System) (405) which is a system used in medical imaging to store, retrieve, distribute, analyze, and digitally process medical images.

System 400 is equipped with a standard network connectivity and Digital Imaging and Communications in Medicine (DICOM) (411) that is a standard for handling, storing, printing, and transmitting information in medical imaging. DICOM includes a file format definition and a network communications protocol.

The E-processor (402) uses the above described network and DICOM connectivity and file format in order to acquire, obtain, view, create, read, write, store, process or, in general, transmit, receive, manage, alter, edit or manipulate images present in the PACS (405) which serves both as an L-source and an H-source. The images stored in the PACS (405) originate from a medical imaging modality (401) such as a CT scanner, an MRI scanner, or a mammography apparatus, etc. The images may also be obtained by the E-processor (402) directly from the medical imaging modality (401). Alternatively or additionally, H-patches may be obtained from a neural network (406) trained by a deep learning algorithm and method.

The E-processor (402) is equipped with enhancement operation elements (410), capable of outputting and/or inputting L-images and/or H-images from and/or to said L-source and/or said H-source, and capable of processing, according to the method of the disclosure, said L-images and/or said H-images as to obtain E-images and, optionally, an E-database (412) for storing the obtained E-images.

The system may further comprise a radiologic workstation (407) communicating with the PACS system (405), for the retrieval of the E-images and their visualization by a physician on display (408) Using an image viewer, for example, a DICOM viewer.

The system may additionally include at least at the radiologic workstation (407) a suitable human-machine interface (HMI) (409) comprising, for example, keyboards and similar peripheral devices, speech-recognition interfaces and so forth.

Optionally, the display (408) capable of displaying L-images, H-images and E-images is, preferably, but not necessarily, a medical diagnostic display.

The elements comprised in the system may be arranged in any suitable combination. For instance, the system may be structured using different devices and components operating in conjunction as described above or may feature different degrees of integration. In an embodiment described hereinafter in the detailed description, the system is integrated in a CT scanner.

Conversely, the system could be adopt a more distributed architecture wherein the E-processor, as well as the H-database and L-database, could be located on cloud based virtual machine and storage.

In an embodiment of the disclosure a system for providing a Locally-Consistent enhancement of a Low-Quality image (L-image) resulting in an Enhanced Image (E-image) may comprise:

an E-processor (402) including enhancement operation elements (410), optionally, including a neural network (406) trained by a deep learning algorithm and method;

a H-database (403) and an L-database (404);

a PACS (Picture Archiving and Communication System) (405) connected through DICOM (411) protocol to E-processor (402), H-database (403) and an L-database (404);

a standard network connection between the E-processor (402), H-database (403) and L-database (404);

a medical imaging modality (401) such as a CT scanner, an MRI scanner, or a mammography apparatus, etc. connected to the E-processor (402);

a radiologic workstation (407) with suitable image viewer and communicating with the PACS system (405), for the retrieval of the E-images and their visualization;

a display (408) preferably, but not necessarily, a medical diagnostic display; and a suitable human-machine interface (HMI) (409).

The elements comprised in the system may be arranged in any suitable combination. For instance, the system may be structured using different devices and components operating cooperating as described above or may feature different degrees of integration. In an embodiment described hereinafter in the detailed description, the system is integrated in a CT scanner. Conversely, the system could be adopt a more distributed architecture wherein the E-processor, as well as the H-database and L-database, could be located on cloud based virtual machine and storage In a further embodiment, the medical imaging system comprises a CT scanner and the L-image is an L-SNR CT-image of an ROI of patient acquired exposing the patient to a relatively low dose of X-ray radiation.

In yet another embodiment, the medical imaging system comprises an MRI scanner and the image is an L-SNR MRI image of an ROI of a patient acquired under scanning conditions resulting in a relatively low SNR image. For example the L-SNR MRI image may have been acquired using a relatively weak magnetic polarizing field, a relatively short scanning period of the patient, and/or for a diffusion weighted MR scan using elevated diffusion weighting values.

BRIEF DESCRIPTION OF FIGURES

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

DETAILED DESCRIPTION

In the detailed discussion below features and operation of a medical imaging system configured in accordance with an embodiment of the disclosure to enhance a L-image to obtain a E-image of a patient are discussed with reference to FIG. 1. Details of a procedure by which the imaging system shown in FIG. 1 may process an L-image of a patient that the imaging system acquires to provide an E-image based on the acquired image, are discussed with reference to FIG. 2. By way of example, the medical imaging system shown in FIG. 1 comprises a CT-scanner. It is noted that in addition to certain imager types mentioned in the specific exemplary embodiments, the imager according to the disclosure may comprise at least one or any combination of more than one of a device suitable for: x-ray radiography, mammography, fluoroscopy, angiography, ultra-sound imaging, positron emission tomography (PET), computed tomography (CT), magnetic resonance imaging (MRI), and any combination thereof.

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which it is intended. Unless otherwise indicated explicitly or implicitly, the word "or" in the description and claims is considered to be the inclusive "or" rather than the exclusive or, and indicates at least one of, or any combination of items it conjoins.

Figure 1A:
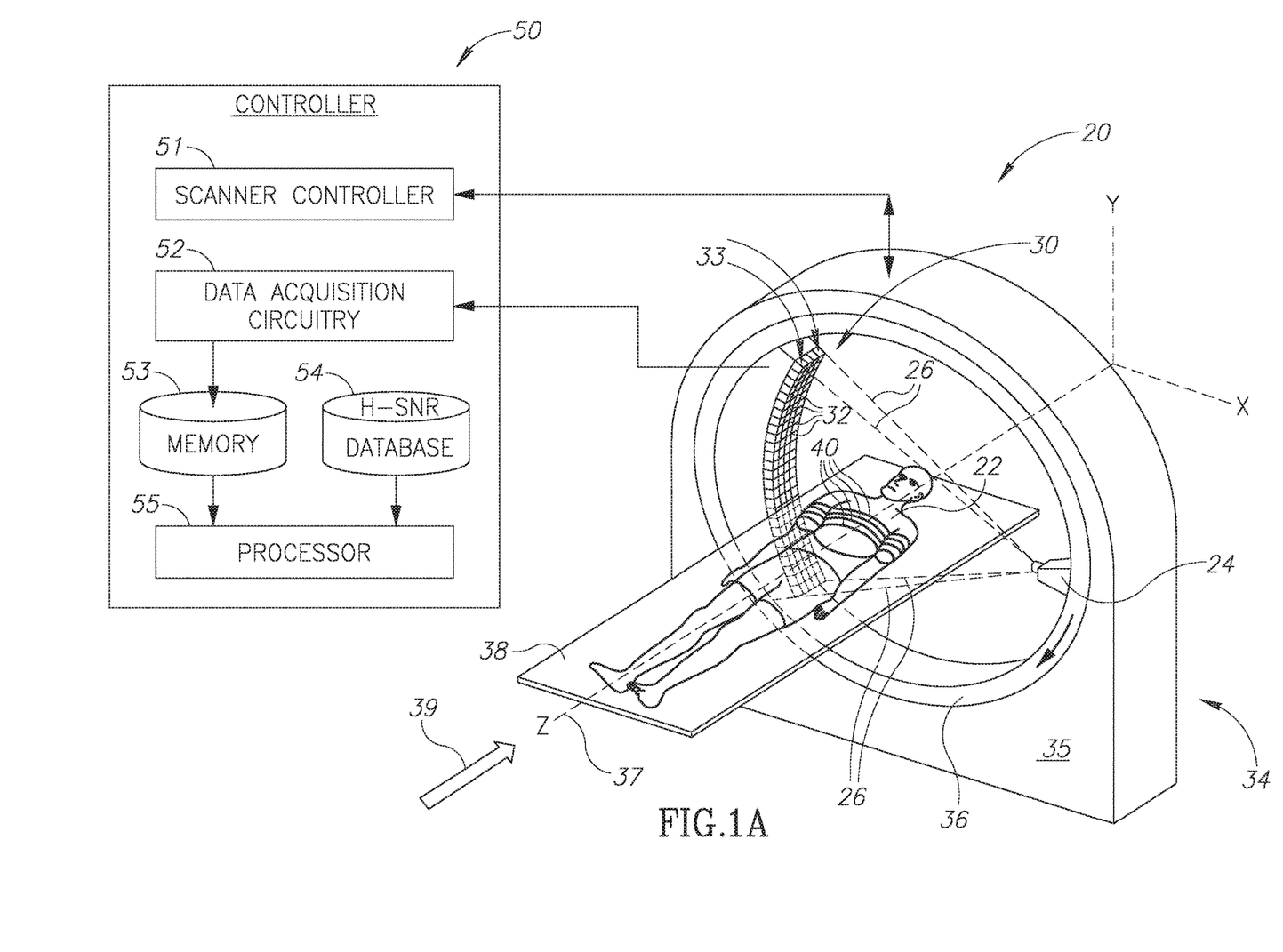
FIG. 1A schematically shows a CT scanner configured to acquire L-SNR CT-images of a patient and process the images to provide enhanced, E-SNR, CT-images of the patient, in accordance with an embodiment of the disclosure.

FIG. 1 schematically shows, in accordance with an embodiment of the disclosure, a multislice CT-scanner 20 configured to acquire low-dose CT-images characterized by a relatively low SNR of patients and process the images to provide enhanced images (E-images), which are characterized by enhanced SNR as well, possibly, by other quality enhancements. In FIG. 1, by way of example, CT-scanner 20 is shown imaging a ROI of the chest of a patient 22.

CT-scanner 20 comprises a gantry 34 having a stator 35 to which a rotor 36 is mounted so that the rotor can be controlled to rotate about an axis 37. An X-ray source 24 controllable to provide an X-ray beam schematically indicated by dashed lines 26 and an array 30 of X-ray detectors 32 opposite the X-ray source are mounted to the rotor. Detectors 32 generate signals that provide measures of intensity of X-rays from X-ray source 24 that pass through a patient imaged by CT-scanner 20. CT-scanner 20 is assumed, by way of example to be a multislice CT-scanner that simultaneously images a plurality of "CT-slices" of the body of a patient and detectors 32 in array 30 are configured in a plurality of contiguous curved rows 33 of the detectors. By way of example, in FIG. 1, for convenience of presentation CT-scanner 20 is shown as controllable to simultaneously image up to four CT-slices of a patient. The patient, such as patient 22, is supported on a couch 38 mounted to a suitable pedestal (not shown) so that the couch is controllable to be translated axially along axis 37 selectively in a direction indicated by a block arrow 39 or in a direction opposite the indicated direction. Detectors 32 in detector array 30 and features of CT-scanner that are shadowed by patient 22 and couch 38, which would not normally be seen in the perspective of FIG. 1, are shown for clarity of presentation by ghost lines.

A controller 50 controls operation of CT-scanner 20 and processing of signals generated by detectors 32 to provide a CT-image of a patient. Controller 50 optionally comprises a scanner controller 51 that controls operation of components of CT-scanner 20, data acquisition circuitry 52, a memory 53, and a processor 55.

Figure 1B:
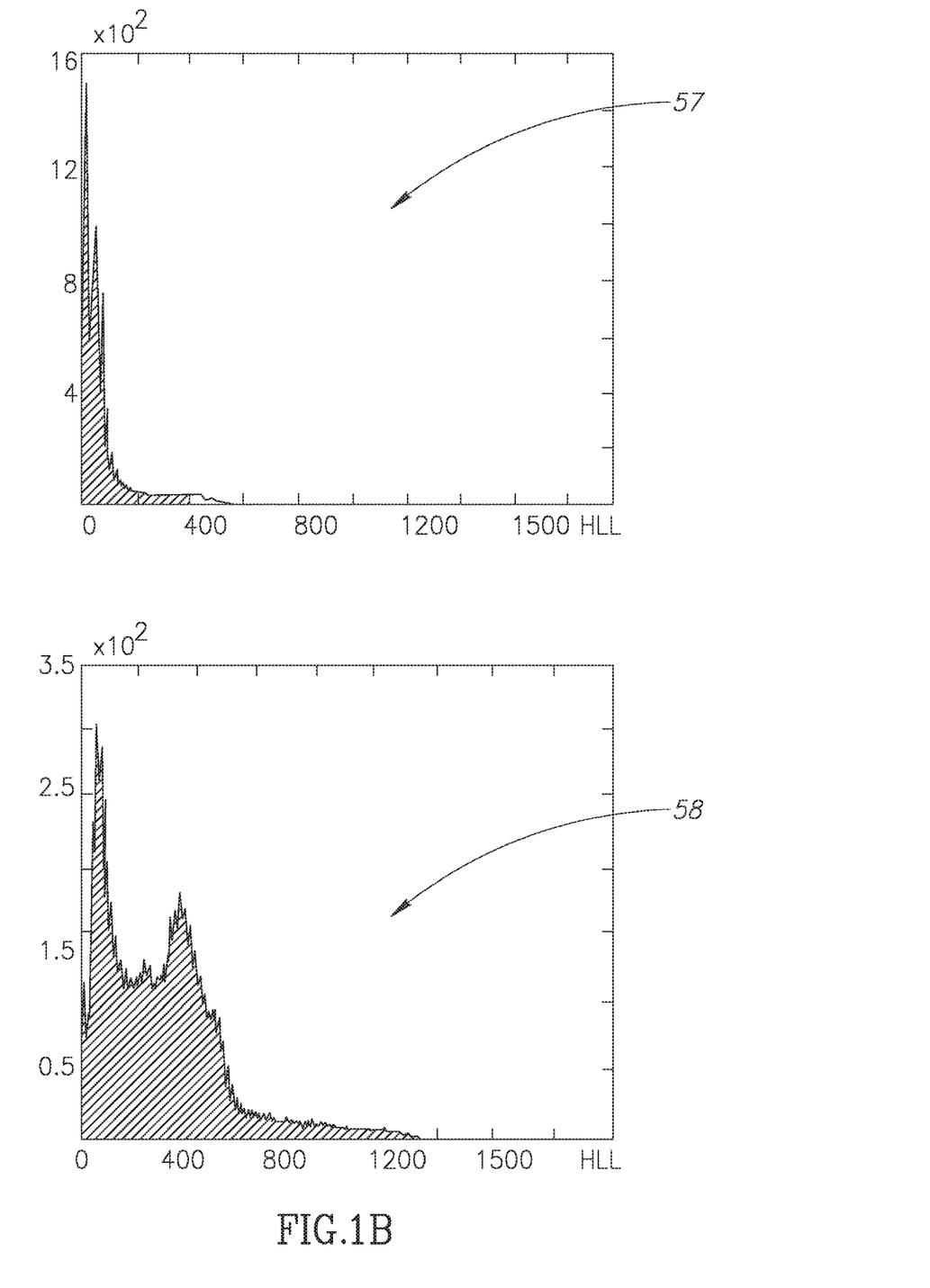
FIG. 1B shows schematic distribution of signal variances of H-Patches optionally comprised in a H-SNR patch database, in accordance with an embodiment of the disclosure.

In an embodiment of the disclosure controller 50 comprises a H-SNR database 54 comprising a plurality of H-SNR images of different regions of a human body for which CT-scanner 20 may be used to acquire images, and/or H-SNR image patches, H-Patches, extracted from H-SNR images for each of different regions of the body for which the CT-scanner may be used to acquire images. In an embodiment H-SNR database 54 comprises H-Patches that have been extracted from H-SNR images and been selected so that a population of H-Patches comprised in the database exhibits a relatively large number of H-Patches having significant information content. Signal variance of an H-patch may be used as a measure of information content of an H-Patch, with relatively large signal variance indicating relatively large information content. Signal variance of an H-Patch refers to a standard deviation of X-ray intensities represented by values, for example gray level values, of the pixels in the H-Patch. In an embodiment, extracted H-Patches are filtered using a roulette wheel selection filter to provide a population of H-Patches exhibiting greater signal variance than a population of extracted H-Patches filtered randomly. By way of example FIG. 1B shows a distribution 57 of a population of H-Patches filtered randomly and a distribution 58 of a population of H-Patches selected using a roulette wheel filter to increase presence of H-Patches having relatively large signal variance in accordance with an embodiment of the disclosure.

Controller 50 may comprise any electronic and/or optical processing and/or control circuitry, to provide and enable functionalities that the controller may require to support its operation in embodiments that are described below and embodiments similar to the described embodiments. By way of example, processor 55 may comprise any one, or any combination of more than one of, a microprocessor, an application specific circuit (ASIC), field programmable array (FPGA) and/or system on a chip (SOC). Memory 53 may comprise any electronic and/or optical circuitry suitable for storing data and/or computer executable instructions and may, by way of example, comprise any one or any combination of more than one of a flash memory, random access memory (RAM), read only memory (ROM), and/or erasable programmable read-only memory (EPROM).

Whereas memory 53, H-SNR database 54, and/or processor 55, are indicated in FIG. 1A as being centralized local modules comprised in CT-scanner 20, at least one of the modules may be a virtual module and/or may be configured as a distributed module comprising hardware and/or software components at different locations outside of CT-scanner 20, and may be cloud based. For example H-SNR database 54 and/or processor 55 may be a cloud based database and controller 50 may comprise and/or have access to any suitable wire and/or a wireless communication interface (not shown) for communicating with the H-SNR database and/or processor.

To image a ROI of a patient's body, such as the chest region of patient 22, system controller 50 controls couch 38 to translate the patient through gantry 34 so that the ROI passes through the gantry. While translating the patient through the gantry, system controller 50 controls X-ray source 24 to generate fan beam 26 and rotor 36 to rotate about axis 37 so that the fan beam exposes the patent to X-rays from a plurality of different "view angles" in a range of about 360° about axis 37. For each of the view angles, detectors 32 provide signals that measure intensities of X-rays in fan beam 26 that pass through the ROI of the patient located between detectors 32 and X-ray source 24. For each view angle rows 33 of detectors 32 provide measurements of X-ray intensity useable to generate images of optionally four different CT-slices of the patient. FIG. 1 schematically shows four exemplary CT-slices 40 of patient 22 for which CT-scanner 20 acquires intensity measurements of X-rays that have passed through patient 22 for the position of patient 22 in gantry 34 and a view angle of about 90° at which X-ray source 24 and detector array 30 are shown in the figure. The intensity signals generated by detectors 32 may be received by data acquisition circuitry 52 which may preprocess and store the preprocessed signals in memory 53. Processor 55 may process the stored signals to generate an image of each slice 40 of patient 22 and combine the images of the CT-slices to provide a 3D volume image of the patient's ROI.

In a variation of the embodiment, processor 55 may first enhance the preprocessed signals stored in memory 53, which signals represent a sinogram of the scan, and then, in order to further increase the quality, the processor may enhance again the image reconstructed from the enhanced sinogram. Either or both of the described enhancements procedures may be carried-out by processor 55 according the flow diagram in FIG. 2 discussed below.

In an embodiment, to moderate risks to the health of patient 22 resulting from exposure of the patient to X-ray radiation from X-ray source 24, controller 50 controls CT-scanner 20 to acquire intensity data for a CT-image of the patient with a relatively low dose of radiation. The CT-image acquired using the low radiation dose may be a L-SNR image characterized by relatively low SNR. Processor 55 may operate to improve SNR of the L-SNR image to generate an image, also referred to as an E-Image, of patient 23 exhibiting enhanced SNR by processing images of CT-slices, such as exemplary CT-slices 40, of the patient using H-Patches stored in database 54.

Figure 2:
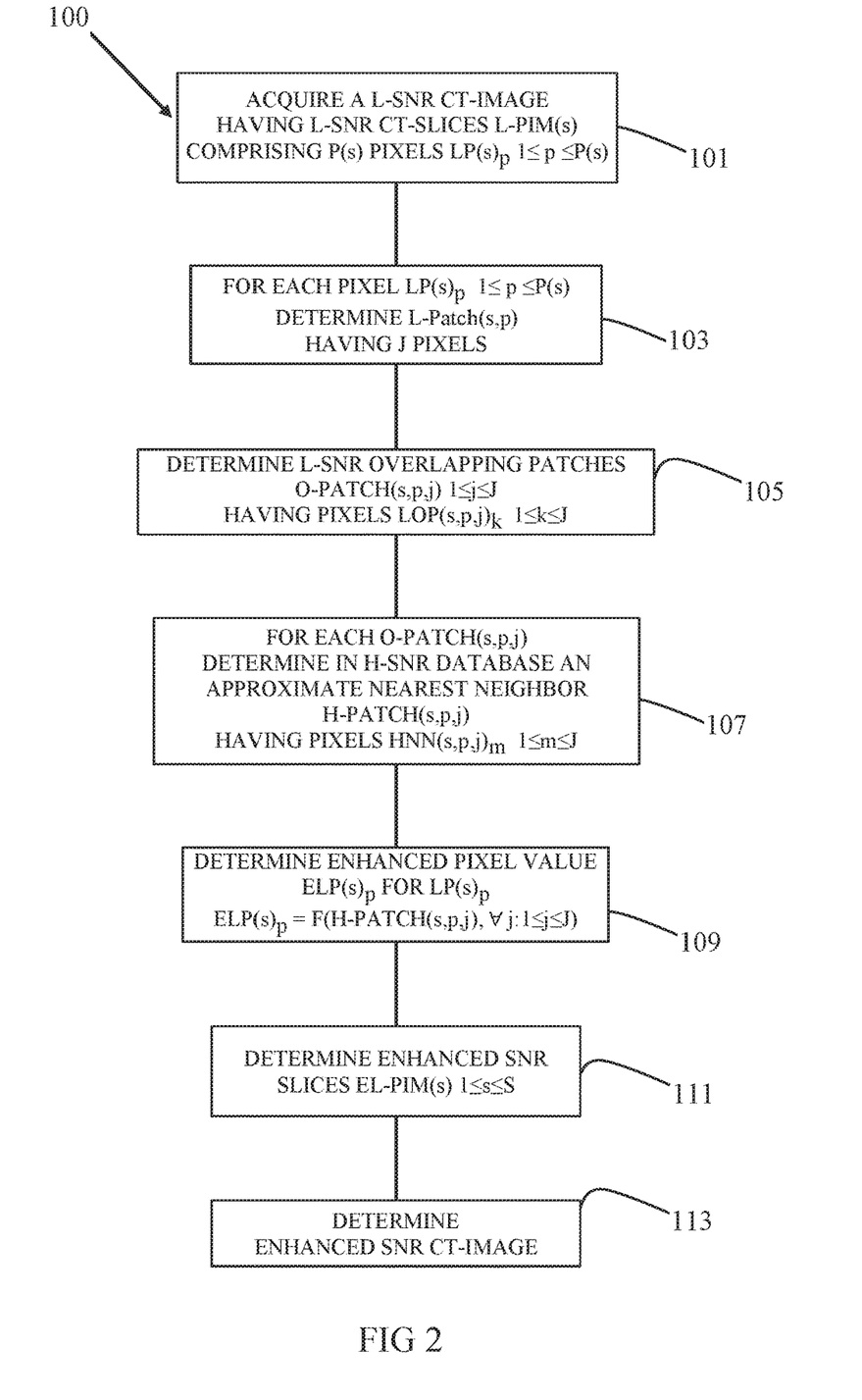
FIG. 2 shows a flow diagram of a procedure that the CT scanner shown in FIG. 1 may use to provide E-SNR images based on L-SNR images, in accordance with an embodiment of the disclosure.

In an embodiment, processor 55 may operate to provide an SNR enhanced CT-image of a ROI of patient 22 in accordance with a procedure illustrated in a flow diagram 100 shown in FIG. 2.

Figure 3A:
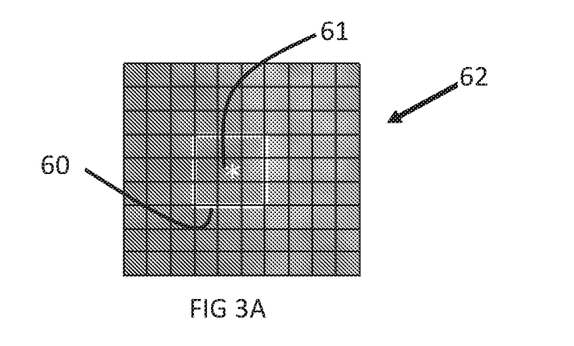
FIG. 3A schematically shows an L-Patch determined for a given pixel in an image of a CT-slice of a patient, in accordance with an embodiment of the disclosure.
Figure 3B:
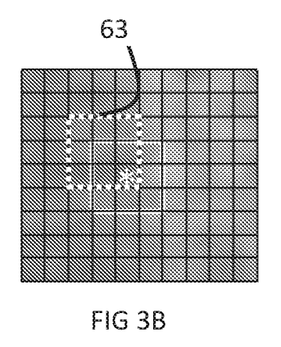
FIGS. 3B-3J schematically show overlapping O-Patches determined for the given pixel and L-Patch shown in FIG. 3A, in accordance with an embodiment of the disclosure.
Figure 3C:
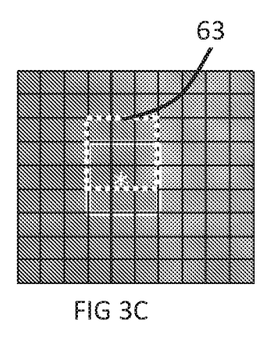
Figure 3D:
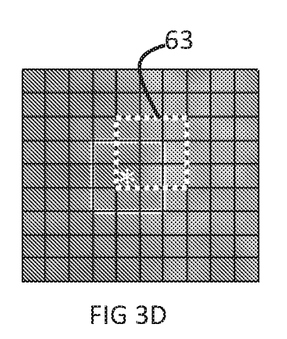
Figure 3E:
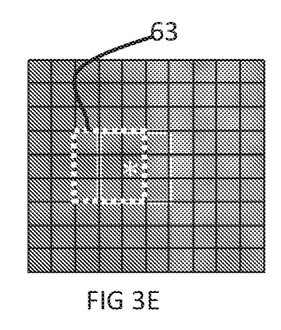
Figure 3F:
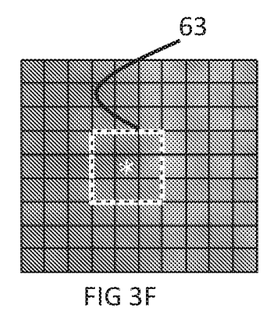
Figure 3G:
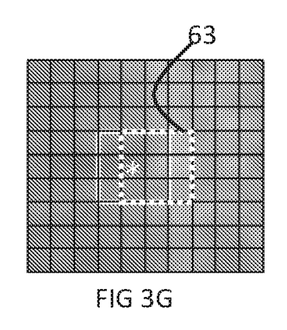
Figure 3H:
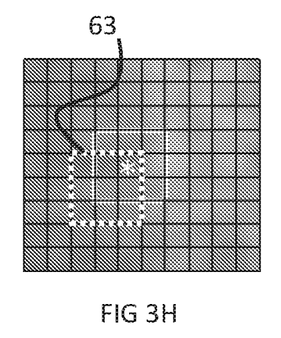
Figure 3I:
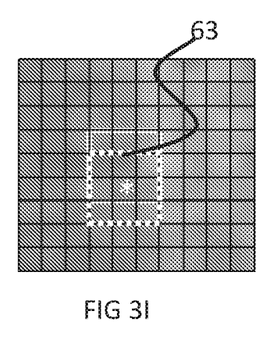
Figure 3J:
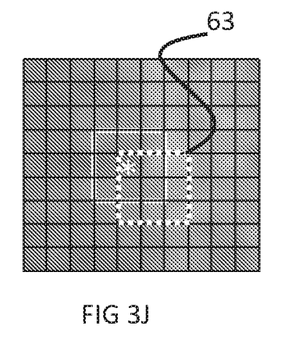

In a block 101 of the procedure, controller 50 controls CT-scanner 20 to acquire a low X-ray dose, L-SNR CT-image of patient 22. The image is assumed to be formed from a number S, of low SNR images, L-PIM(s), $1 \leq s \leq S$, of CT-slices of the patient, each slice comprising pixels $LP(s)_p$ $1 \leq p \leq P(s)$. In a block 103 processor 55 (FIG. 1A) optionally determines for each pixel $LP(s)_p$ in an image L-PIM(s) of an s-th CT-slice, an L-Patch(s,p) comprising and optionally centered on pixel $LP(s)_p$, and comprising J pixels in image L-PIM(s). Optionally, L-Patch(s,p) is square. FIG. 3A schematically shows an example square L-Patch(s,p) 60 outlined in a white border and comprising J=9 pixels defined for an $LP(s)_p$ pixel 61 marked by an asterisk in an image L-PIM(s)

62 of an s-th CT-slice of patient 22. Optionally, in a block 105 the processor determines J different patches O-Patch(s, p,j), 1≤j≤J, in image L-PIM(s) 62 that overlap L-Patch(s,p) 60, each O-Patch(s,p,j) comprising a different set of J pixels from image L-PIM(s). The pixels in a given overlapping O-Patch(s,p,j) may be referred to as pixels LOP(s,p,j)$_k$, 1≤k≤J. FIGS. 3B-3J schematically show the J=9 overlapping patches O-Patch(s,p,j), in L-PIM(s) 62 defined for L-Patch (s,p) 60 shown in FIG. 3A. Each overlapping patch O-Patch (s,p,j) is bordered by a dashed white border 63, and comprises a different set of J=9 pixels from CT-slice image L-PIM(s) 62, one of which pixels is coincident with pixel 61 indicated by the asterisk.

Optionally, in a block 107, processor 50 identifies for each O-Patch(s,p,j) 63 a high SNR patch H-Patch(s,p,j) in H-SNR database 54 (FIG. 1A) having a same number of pixels and same shape as O-Patch(s,p,j) that exhibits a relatively high degree of similarity with the O-Patch(s,p,j). In an embodiment the identified H-patch(s,p,j) may be an approximate nearest neighbor (ANN) to the O-Patch(s,p,j). An approximate nearest neighbor may be determined using any of various nearest neighbor search algorithms and may for example be determined using a randomized kd-trees algorithm such as implemented in the Fast Library for ANN (FLANN) for a Euclidean norm. Alternatively, a high SNR patch for a given O-Patch(s,p,j) may be generated by a regression neural network trained to generate a high SNR patch when fed at its input with a low SNR patch. For this purpose, it is necessary to have a training set consisting of corresponding low and high SNR patch pairs. Said pairs of patches can be obtained using an ANN algorithm to associate between patches from a low SNR database to patches of a high SNR database. Alternatively, the pairs can be created by adding synthetic noise corresponding to a given probability distribution function depending on the considered imaging modality (for example, Rician noise for MRI, Gaussian and Poisson noise for CT). In a block 109, processor 55 determines an enhanced value ELP(s)$_p$ for each pixel LP(s)$_p$ as a function of pixel values of pixels in the approximate nearest neighbor high SNR H-Patches(s,p,j), identified for the overlapping patches, O-Patches(s,p,j), 1≤j≤J, associated with LP(s)$_p$. In symbols ELP(s)$_p$=F(H-Patch(s,p,j) ∀ j:1≤j≤J)).

Let the pixels in a j-th approximate nearest neighbor H-Patch(s,p,j) identified for an O-Patch(s,p,j) be represented by HNN(s,p,j)$_m$, 1≤m≤J and its value by Val(HNN'(s,p,j)$_m$). Let a pixel HNN(s,p,j)$_m$ for which m=m*(j) be a pixel, hereinafter also referred to as a H-SNR coincident pixel, in H-Patch(s,p,j) that is homologous with a pixel LOP(s,p,j)$_k$ in overlapping patch O-PATCH(s,p,j) that is coincident with pixel LP(s)$_p$ in L-PIM(s). ELP(s)$_p$ may optionally be determined in accordance with an expression ELP(s)$_p$=F(H-Patch (s,p,j))=(1/J)Σ$_1^J$ Val(HNN(s, p, j)$_{m*(j)}$). A similar way to express the enhanced value for the pixel is $$ELP(s)_p = \hat{p}_j = \frac{1}{P_S^2}\sum_{i=1}^{P_S^2} \hat{P}_{i_j} \text{ as for } \hat{P}_i \in (NN_{P_j})$$

already given in the summary.

In an embodiment, the enhanced pixel ELP(s)$_p$ is determined as a function of the HNN(j)$_{m*(j)}$ weighted by a measure of similarity between the L-PATCH(s,p) determined for LP(s)p and H-PATCH(j) to which pixel HNN(j)$_{m*(j)}$ belongs. If D(s,p,j) represents a measure of similarity between L-PATCH(s,p) and H-PATCH(j) then ELP(s)$_p$ may be determined in accordance with an expression, ELP(s)$_p$=F(Val(HNN(s,p,j)$_{m*(j)}$))= [Σ$_1^J$Val(HNN(j)$_{m*(j)}$)exp(D(s,p,j)/h²))]/Σ$_1^J$ exp(D (s,p,j)/h², where h=Jγ and γ is a constant. The Similarity function D can alternatively be replaced by a Distance function D' for which D'=Q−D, where Q is a positive constant number. In that case, a similar formulation for ELP(s)$_p$ can be given by $$ELP(s)_p = \hat{p}_j = \frac{\sum_{i=1}^{P_S^2} \exp\left(-\frac{D(P_j, \hat{P}_i)}{h^2}\right)\hat{P}_{i_j}}{\sum_{i=1}^{P_S^2} \exp\left(-\frac{D(P_j, \hat{P}_i)}{h^2}\right)}, \hat{P}_i \in (NN_{P_j}),$$

as already given in the summary.

In a block 111 processor 55 uses the enhanced pixel values ELP(s)$_p$ determined for each CT-slice image L-PIM(s) to provide a CT-slice image EL-PIM(s) having enhanced SNR. The processor uses the CT-slice images EL-PIM(s) for all the S CT-slices, optionally in a block 113, to provide an E-SNR CT-image of patient 22 having an SNR that is enhanced relative to the SNR of the originally acquired L-SNR CT-image of patient 22.

It is noted that the above description of FIGS. 1A-3 describes embodiments of the disclosure with reference to processing CT-slices acquired by CT-scanners, however, as noted above practice of an embodiment of the disclosure is not limited to CT-scanners and CT-slices. For example, an embodiment of the disclosure may be configured to process sinogram images acquired by a CT-scanner prior to the sinograms being processed to provide images of CT-slices of a patient. For example, H-SNR database 54 may comprise high SNR sinograms and/or sinogram H-Patches extracted from high SNR sinograms. Processor 55 may process low SNR sinograms of CT-slices of patient 22 acquired by CT-scanner 20 using sinogram H-Patches in a procedure similar to procedure 100 to provide high SNR sinograms for patient 22. The high SNR sinograms may then be processed to provide a picture CT-image of patient 22 having an SNR that is enhanced relative to an SNR of a CT-image of the patient that might have been provided using the L-SNR sinograms. And systems and methods in accordance with embodiments of the disclosure may be configured to enhance for example, low-SNR satellite images, subsurface Earth images acquired for example using seismic tomography, or ultrasound images of the human body or of inanimate bodies.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the disclosure in the present application are provided by way of example and are not intended to limit the scope of the disclosure. The described embodiments comprise different features, not all of which are required in all embodiments. Some embodiments utilize only some of the features or possible combinations of the features. Variations of embodiments of the disclosure that are described, and embodiments comprising different combinations of features noted in the described embodiments, will occur to persons of the art.

The invention claimed is:

1. A method for providing a Locally-Consistent enhancement of a Low-Quality image (L-image) of a ROI to provide an Enhanced Image (E-image) of the ROI, wherein F(•) returns an enhanced pixel value EPV="$\hat{p}_j$" for the given pixel $p_j$ that is computed as a function of H-patches belonging to a set $\{NNp_j\}$ of nearest neighbor H-patches, $\hat{P}_i$, $1 \le i \le P_N$, where $P_N$ is a number of pixels in the L-patch, the method further comprising:
   selecting a pixel $p_j$ of the L-image to be enhanced;
   (ii) defining a patch (L-patch) in the L-image, having $P_N$ pixels and comprising pixel $p_j$;
   (iii) defining $P_N$ O-patches that have the same size as the L-patch, contain pixel $p_j$ and overlap at least a portion of the L-patch;
   (iv) for each O-patch, returning from a relevant high-quality source (H-source), a high quality patch (H-patch) that satisfies a desired similarity criterion wherein the H-patches and L-images are acquired from different imaging systems;
   (v) computing an enhanced pixel value (EPV) for $p_j$, based on F(•); and
   (vi) replacing the pixel value of $p_j$ with the computed EPV.

2. A method for providing a Locally-Consistent enhancement of a Low-Quality image (L-image) of a ROI to provide an Enhanced Image (E-image) of the ROI, wherein function (•) returns an average value of pixels from the H-patches that are homologous with a pixel in an O-patch coincident with the given pixel, in symbols $$\hat{p}_j = F(\cdot) = \frac{1}{P_S^2} \sum_{i=1}^{P_N} \hat{P}_{i_j} \text{ for } \hat{P}_i \in \{NNp_j\}.$$

the method further comprising:
   (i) selecting a pixel pj of the L-image to be enhanced;
   (ii) defining a patch (L-patch) in the L-image, having PN pixels and comprising pixel $p_j$;
   (iii) defining $P_N$ O-patches that have the same size as the L-patch, contain pixel $p_j$ and overlap at least a portion of the L-patch;
   (iv) for each O-patch, returning from a relevant high-quality source (H-source), a high quality patch (H-patch) that satisfies a desired similarity criterion wherein the H-patches and L-images are acquired from different imaging systems;
   (v) computing an enhanced pixel value (EPV) for $p_j$, based on function (•); and
   (vi) replacing the pixel value of $p_j$ with the computed EPV.

3. A method for providing a Locally-Consistent enhancement of a Low-Quality image (L-image) of a ROI to provide an Enhanced Image (E-image) of the ROI, wherein function F(·) returns a sum of $\hat{P}_i$, i=1 ... $P_N$ weighted by a distance measure between the overlapping pixels of $\hat{P}_i$ and the original L-patch defined for the given pixel $p_j$, formalized as follows:

$$\hat{p}_j = \frac{\sum_{i=1}^{P_N} \text{EXP}\left(-\frac{D(P_j, \hat{P}_i)}{h^2}\right) \hat{P}_{i_j}}{\sum_{i=1}^{P_S^2} \text{EXP}\left(-\frac{D(P_j, \hat{P}_i)}{h^2}\right)}, \hat{P}_i \in \{NNp_j\}.$$

the method further comprising:
   (i) selecting a pixel $p_j$ of the L-image to be enhanced;
   (ii) defining a patch (L-patch) in the L-image, having $P_N$ pixels and comprising pixel $P_j$;
   (iii) defining $P_N$ O-patches that have the same size as the L-patch, contain pixel $p_j$ and overlap at least a portion of the L-patch;
   (iv) for each O-patch, returning from a relevant high-quality source (H-source), a high quality patch (H-patch) that satisfies a desired similarity criterion wherein the H-patches and L-images are acquired from different imaging systems;
   (v) computing an enhanced pixel value (EPV) for $p_j$, based on function F(•); and
   (vi) replacing the pixel value of $p_j$ with the computed EPV.

4. A system for providing an Enhanced Image (E-image) of a ROI based on a Locally-Consistent enhancement of a Low-Quality image (L-image) of the ROI, the system comprising:
   (i) an E-processor having enhancement operation elements, that include set of instructions executable to implement a trained neural network said enhancement comprising:
      a) selecting a pixel $p_j$ of the L-image to be enhanced;
      b) defining a patch (L-patch) in the L-image, having $P_N$ pixels and comprising pixel $p_j$;
      c) defining $P_N$ O-patches that have the same size as the L-patch, contain pixel $p_j$, and overlap at least a portion of the L-patch;
      d) for each O-patch, returning from a relevant high-quality source (H-source), a high quality patch (H-patch) that satisfies a desired similarity criterion;
      e) computing an enhanced pixel value (EPV) for $p_j$ based on a function F(•) of the H-patches; and
      f) replacing the pixel value of $p_j$ with the computed EPV;
   (ii) a H-database and an L-database;
   (iii) a PACS (Picture Archiving and Communication System) connected through DICOM protocol to E-processor, H-source and an L-database;
   (iv) a medical imaging modality connected to the E-processor;
   (v) a radiologic workstation communicating with the PACS system, for the retrieval of the E-images and their visualization;
   (vi) a display; and
   (vii) a human-machine interface (HMI).

5. Claim according to claim 1 and comprising repeating steps (i) to (vi).

6. Claim according to claim 2 and comprising repeating steps (i) to (vi).

7. Claim according to claim 3 and comprising repeating steps (i) to (vi).

8. Claim according to claim 4 and comprising repeating steps (a) to (f).

* * * * *